United States Patent
Prasad et al.

(10) Patent No.: US 10,238,112 B1
(45) Date of Patent: Mar. 26, 2019

(54) FLUCARBAZONE SODIUM HEMIHYDRATE METHOD AND COMPOSITION

(71) Applicant: ARYSTA LIFESCIENCE INC., Cary, NC (US)

(72) Inventors: Vic Prasad, Leawood, KS (US); Christopher L. Larson, Cary, NC (US); Cameron Seath Gibb, Apex, NC (US)

(73) Assignee: Arysta LifeScience Inc., Cary, NC (US)

( * ) Notice: Subject to any disclaimer, the term of this patent is extended or adjusted under 35 U.S.C. 154(b) by 0 days.

(21) Appl. No.: 15/879,073

(22) Filed: Jan. 24, 2018

(51) Int. Cl.
| | | |
|---|---|---|
| *A01N 25/04* | (2006.01) | |
| *A01N 41/06* | (2006.01) | |
| *A01N 43/653* | (2006.01) | |

(52) U.S. Cl.
CPC .......... *A01N 43/653* (2013.01); *A01N 25/04* (2013.01); *A01N 41/06* (2013.01)

(58) Field of Classification Search
None
See application file for complete search history.

(56) References Cited

U.S. PATENT DOCUMENTS

| | | |
|---|---|---|
| 6,147,221 A | 11/2000 | Prasad et al. |
| 6,147,222 A | 11/2000 | Prasad et al. |
| 6,160,125 A | 12/2000 | Prasad et al. |

*Primary Examiner* — Alton N Pryor
(74) *Attorney, Agent, or Firm* — Greenblum & Bernstein, P.L.C.

(57) ABSTRACT

A flucarbazone sodium hemihydrate method and composition. A method of suppressing growth of grass and broadleaf weeds is described including applying to said weeds at least one dust-free composition comprising flucarbazone sodium-hemihydrate as an active ingredient. A method for preparing flucarbazone sodium-hemihydrate is also described including treating 4,5-dihydro-3-methoxy-4-methyl-5-oxo-N-[[2-(trifluoromethoxy)phenyl]sulfonyl]-1H-1,2,4-triazole-1-carboxamide (MSU) with aqueous sodium hydroxide under pH-controlled conditions; and confirming that a hemihydrate flucarbazone sodium of the following formula:

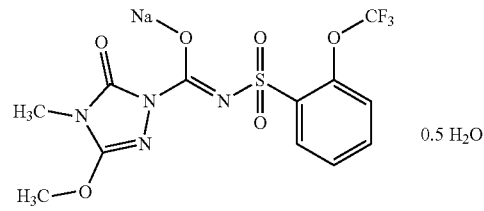

has been obtained.

1 Claim, 3 Drawing Sheets

FLUCARBAZONE SODIUM HEMIHYDRATE METHOD AND COMPOSITION

TECHNICAL FIELD

The field of art to which this invention generally pertains is herbicidal compositions and methods of making and using the same.

BACKGROUND

Sulfonylaminocarbonyl triazolinones are well known in the art, as are processes for their preparation and use as herbicides. However, isolation of salts of these materials from anhydrous conditions for use as herbicides results in a product which is very dusty and difficult to handle during formulation.

Accordingly, there is a constant search in this area for improvements to these products in all areas, including improvements in safety handling.

BRIEF SUMMARY

A method of suppressing growth of grass and broadleaf weeds is described comprising applying to said grass and weeds at least one dust-free composition comprising flucarbazone sodium-hemihydrate as an active ingredient.

A method for preparing flucarbazone sodium-hemihydrate is also described comprising treating 4,5-dihydro-3-methoxy-4-methyl-5-oxo-N-[[2-(trifluoromethoxy)phenyl]sulfonyl]-1H-1,2,4-triazole-1-carboxamide (MSU) with aqueous sodium hydroxide under pH-controlled conditions; and confirming that a hemihydrate flucarbazone sodium of the following formula:

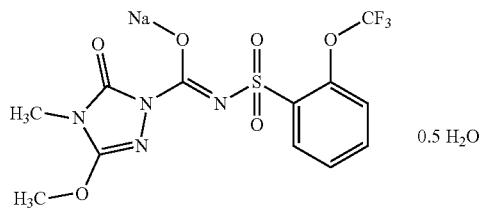

has been obtained.

Additional embodiments include: the process described above where the treatment is carried out at a temperature of from about —20° C. to about 120° C.; the process described above where the treatment is carried out at a temperature of from about 0 C. to about 45° C. (e.g., including 0° C., 5° C., 10° C., 15° C., 20° C., 25° C., 30° C., 35° C., 40° C., and 45° C.); the process described above where the treatment is carried out at a pH of about 5 to about 10; the process described above where the treatment is carried out at a pH of about 5.5 to about 9; and the process described above where the treatment is carried out at a pH of about 6 to about 7.

These, and additional embodiments, will he apparent from the following descriptions.

DETAILED DESCRIPTION

Figure 1:
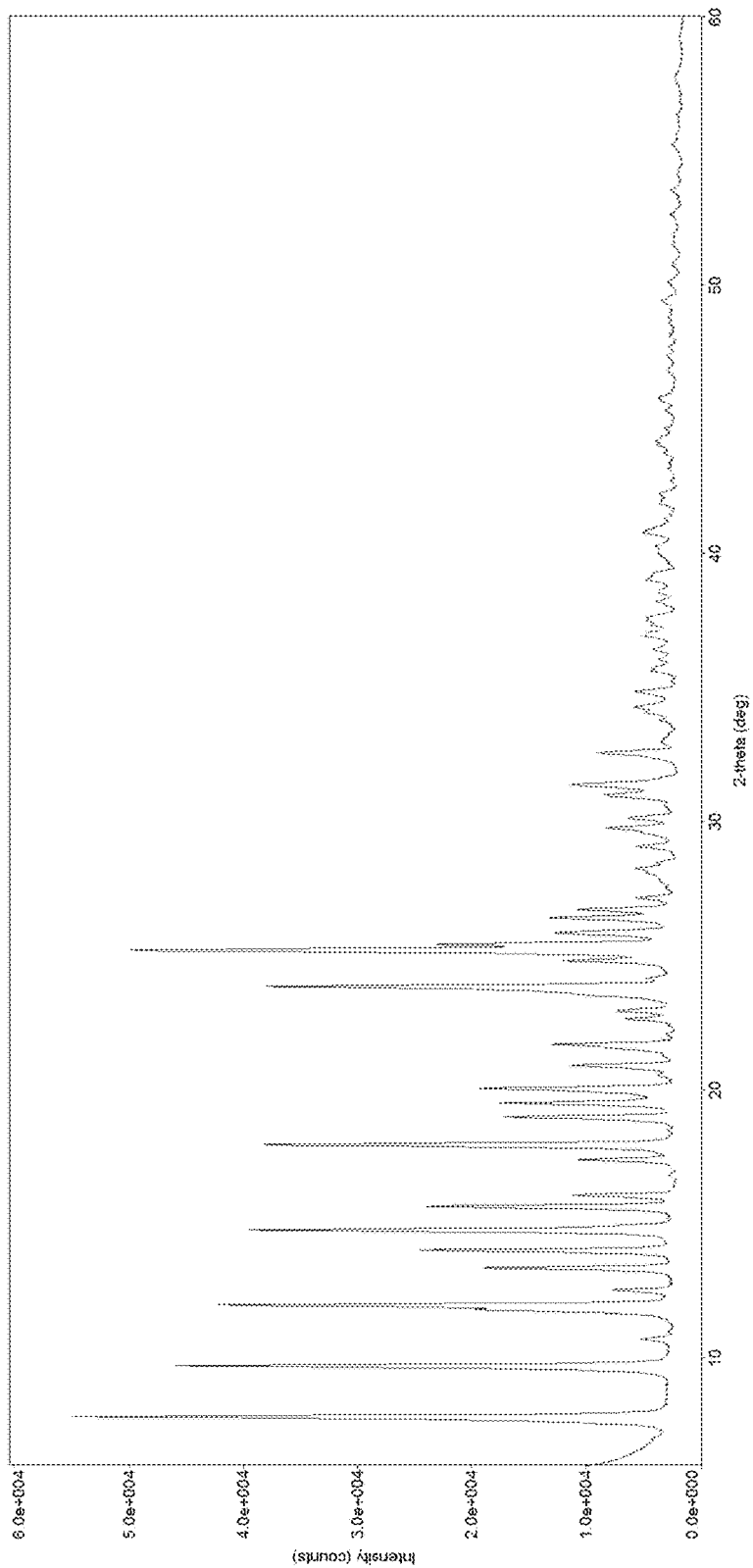
FIG. 1 shows measured x-ray diffraction patterns.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, he embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to he limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Manufacturing processes for flucarbazone sodium and structurally related propoxycarbazone sodium have been described in U.S. Pat. Nos. 6,147,221; 6,147,222; and 6,160,125, the disclosures of which are incorporated herein by reference in their entirety. Both products may be formed by deprotonation of the parent sulfonylurea in the presence of aqueous sodium hydroxide. However, of the two, only flucarbazone sodium forms a stable hydrate under the reaction conditions described therein. Based upon routine analyses of hundreds of samples in the past, the profiles indicated about 94% Flucarbazone-Na and about 4% $H_2O$. These numerical values pointed to Flucarbazone-Na. 1 $H_2O$, that is, a mono-hydrate. However, it has now been found through single crystal X-ray analysis, that by controlling the above-described processes as described herein, the reaction product unexpectedly forms a hemihydrate of chemical formula $C_{12}H_{11}F_3N_4O_{6.5}S$ when crystallized from aqueous systems. It is also believed that the bulk active ingredient is in one crystal form. In order to attain the crystal structure desired it is critical that during the conversion step of the sulfonylaminocarbonyl triazolinone intermediate product to a salt that the reaction is carried out under pH controlled conditions wherein the base is added to the reaction mixture in an amount such that the pH of the mixture attained is from about 5 to about 10, preferably from about 5.5 to about 9, and most preferably from about 6to about 7.

Delivery of a solid form of flucarbazone sodium which can be readily formulated is important for widespread applications. Flucarbazone-sodium is a highly active herbicide and safe handling for such a product is very important. Isolation of hydrated flucarbazone sodium as described herein provides access to such an easily formulated product. The conventional anhydrous form is dusty and not easily formulated. The flucarbazone sodium is formed by treatment of MSU with aqueous sodium hydroxide under the pH controlled conditions described above. Because it is a two phase reaction stirring is critical. The product crystallizes directly from the mixture and is collected by filtration then dried. Single crystal x-ray analysis confirms the formation of the product as a hemihydrate.

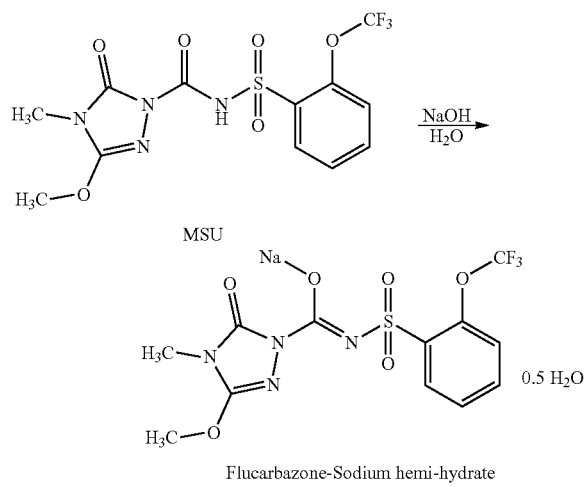

Flucarbazone-Sodium hemi-hydrate

During reaction with aqueous NaOH, solvents such as MIBK (methyl isobutyl ketone), toluene, and/or xylene can also be employed, with MIBK being preferred.

In addition to the some of the benefits mentioned above, other representative benefits include reduction in potential dust explosion properties as well as operator industrial hygiene improvements from exposure and handling advantages. There are also resource benefits from associated with not having to dry to anhydrous form for stripping out solvents, and equipment efficiency and from formulation handling (dust loss), all with their potential to realize their associated economic benefits as well. Representative grasses which can be suppressed and/or controlled include: green foxtail, wild oat, volunteer tame oat, barnyardgrass, windgrass, cheat (true cheat), California brome, Japanese brome, rattail fescue, downy brome, rescuegrass, Italian ryegrass, Persian darnel, yellow foxtail, common millet, yellow bristle-grass, ryegrass, black grass, and foxtail barley. Representative broadleaf weeds which can be suppressed and/or controlled include redroot pigweed, wild mustard, black mustard, blue mustard, field pennycress, fixweed, lady's thumb, Pennsylvania smartweed, shepherd's purse, tansy mustard, tumble mustard, volunteer canola, black nightshade, black bindweed, hemp nettle, green smartweed, stinkweed, and wild buckwheat.

EXAMPLES

In FIG. 1, the x-ray diffraction pattern was measured using data collected on a Bruker D2Phaser in theta-theta geometry using Cu (Kα1/Kα2) radiation and a Ni Kβ filter (detector side). Additional beam optics and settings: primary and secondary axial Soller slits)(2.5°), fixed 0.6 mm divergence slit, 1 mm anti-scatter-screen, Detector: 1D LYNX-EYE with a 5° window, Generator: 30 kV, 10 mA, The software was DIFFRAC.SUITE COMMANDER, Bruker AXS. DIFFRAC.EVA 2.1, Bruker AXS (2010-2012). PDXL2 Version 2,4.2.0, Rigaku Corporation (2007-2015).

Figure 2:
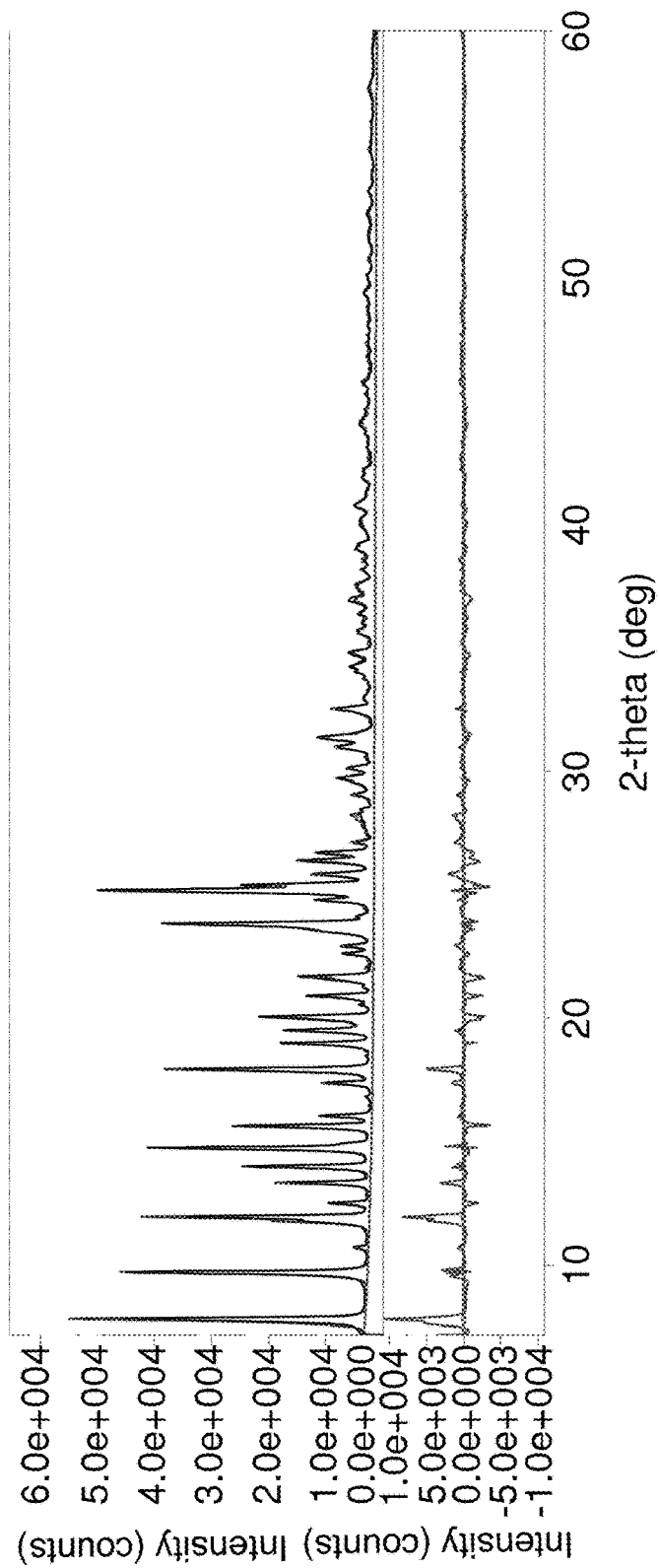
FIG. 2 shows single crystal structure input.

In FIG. 2, the x-ray diffraction pattern was measured with Rietveld it using single crystal structure as input. The data shows that the bulk material is 100% the same as the single crystal structure, with no indications of other phases or impurities.

Figure 3:
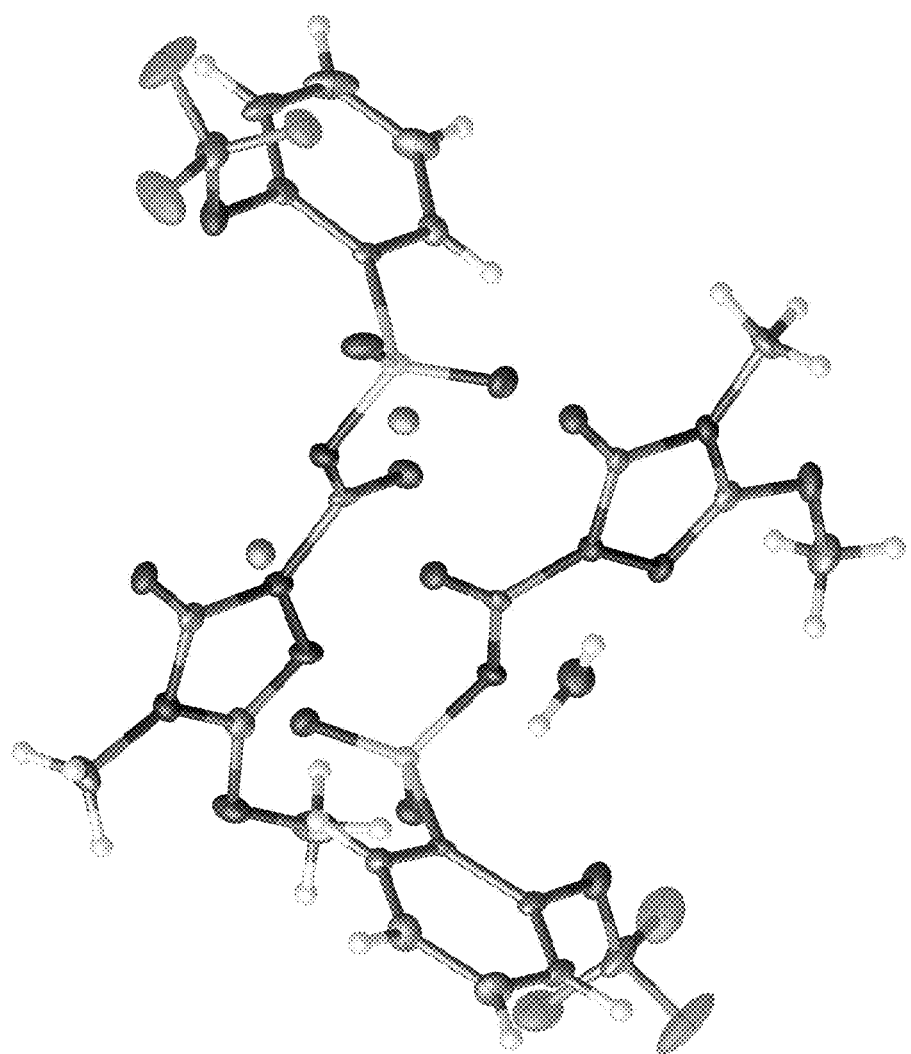
FIG. 3 shows thermal ellipsoids.

FIG. 3 demonstrates thermal ellipsoids drawn at the 50% probability level. Tables 1 and 2 demonstrate the typical parameters measured.

TABLE 1

| Formulas | | $C_{12}H_{11}F_3N_4NaO_{6.5}S$ $C_{12}H_{10}F_3N_4O_6S,Na,0.5(H_2O)$ | |
| --- | --- | --- | --- |
| $D_{calc}/g\ cm^{-3}$ | 1.773 | Wavelength/Å | 0.71073 |
| $\mu/mm^{-1}$ | 0.309 | Radiation type | MoK$_\alpha$ |
| Formula weight | 427.30 | $\Theta_{min}/°$ | 2.304 |
| Color | Clear colorless | $\Theta_{max}/°$ | 28.499 |
| Shape | prism | Measured Refl. | 12063 |
| Size/mm$^3$ | 0.10 × 0.04 × 0.03 | Independent Refl. | 12063 |
| T/K | 100(2) | Reflections Used | 10838 |
| Space Group | P2$_1$/c | Parameters | 507 |
| a/Å | 22.7820(8) | Restraints | 3 |
| b/Å | 9.6327(3) | Largest Peak | 0.402 |
| c/Å | 14.9502(5) | Deepest Hole | −0.328 |
| α/° | 90 | GooF | 1.077 |
| β/° | 102.576(4) | wR$_2$ (all data) | 0.1369 |
| γ/° | 90 | wR$_2$ | 0.1327 |
| V/Å$^3$ | 3202.14(19) | R$_1$ (all data) | 0.0625 |
| Z | 8 | R$_1$ | 0.0540 |
| Z' | 2 | | |

TABLE 2

Fractional Atomic Coordinates (×10$^4$) and Equivalent Isotropic Displacement Parameters (Å$^2$ × 10$^3$) for 2017seas0057_R1_100K_twin1_hklf4. $U_{eq}$ is defined as ⅓ of the trace of the orthogonalised $U_{ij}$.

| Atom | x | y | z | $U_{eq}$ |
| --- | --- | --- | --- | --- |
| C101 | 7718.9(16) | −994(3) | 2120(2) | 14.0(7) |
| C102 | 8079.6(17) | −1177(4) | 875(2) | 15.8(7) |
| C103 | 8630.7(18) | −2451(4) | 2266(3) | 23.3(8) |
| C104 | 8399.4(19) | −992(5) | −487(3) | 28.7(9) |
| C105 | 6902.3(15) | 685(4) | 1355(2) | 12.9(6) |
| C106 | 5630.9(15) | 1357(3) | 1901(2) | 11.0(6) |

TABLE 2-continued

Fractional Atomic Coordinates (×10⁴) and
Equivalent Isotropic Displacement Parameters
($Å^2 \times 10^3$) for 2017seas0057_R1_100K_twin1_hklf4.
$U_{eq}$ is defined as ⅓ of the trace of the orthogonalised $U_{ij}$.

| Atom | x | y | z | $U_{eq}$ |
|---|---|---|---|---|
| C107 | 5328.5(16) | 1700(4) | 1027(2) | 16.3(7) |
| C108 | 4772.3(18) | 1138(5) | 674(3) | 26.1(9) |
| C109 | 4522.6(19) | 217(5) | 1173(3) | 30.8(10) |
| C110 | 4818.1(19) | −147(4) | 2042(3) | 26.0(9) |
| C111 | 5368.2(17) | 439(4) | 2398(2) | 15.7(7) |
| C112 | 5457(2) | 533(4) | 3974(3) | 25.5(9) |
| C201 | 6962.4(15) | 5702(3) | 2567(2) | 12.1(6) |
| C202 | 6887.8(16) | 6303(3) | 1130(2) | 14.6(7) |
| C203 | 6189.5(17) | 7478(4) | 1990(3) | 20.8(8) |
| C204 | 6925(2) | 6662(4) | −391(3) | 25.3(9) |
| C205 | 7736.8(15) | 3907(3) | 2529(2) | 12.1(6) |
| C206 | 9176.6(15) | 3330(3) | 2760(2) | 12.2(6) |
| C207 | 9428.9(16) | 3063(4) | 3663(2) | 15.2(7) |
| C208 | 9923.4(18) | 3798(4) | 4103(3) | 21.8(8) |
| C209 | 10162.3(18) | 4828(4) | 3649(3) | 24.0(8) |
| C210 | 9900.1(17) | 5131(4) | 2753(3) | 20.5(8) |
| C211 | 9414.1(16) | 4378(4) | 2318(2) | 14.5(7) |
| C212 | 9412(2) | 4553(4) | 761(3) | 26.3(9) |
| F101 | 4955.3(16) | −118(3) | 4036(2) | 49.8(8) |
| F102 | 5862.2(14) | 343(3) | 4726.0(17) | 44.9(8) |
| F103 | 5317.8(11) | 1848(2) | 3904.8(15) | 26.1(5) |
| F201 | 9798.1(16) | 5577(3) | 757.4(19) | 52.2(9) |
| F202 | 9024.3(14) | 4579(3) | −24.0(16) | 39.1(7) |
| F203 | 9724.6(13) | 3390(3) | 813.7(18) | 36.7(6) |
| N101 | 8155.3(14) | −1600(3) | 1755(2) | 14.8(6) |
| N102 | 7626.6(13) | −375(3) | 611.3(19) | 13.8(6) |
| N103 | 7395.7(13) | −235(3) | 1397.9(19) | 13.3(6) |
| N104 | 6833.4(13) | 1007(3) | 2197.5(19) | 13.7(6) |
| N201 | 6660.1(14) | 6540(3) | 1884(2) | 14.0(6) |
| N202 | 7311.2(13) | 5408(3) | 1247.9(18) | 13.1(6) |
| N203 | 7378,5(13) | 5041(3) | 2171.6(18) | 113(6) |
| N204 | 8028.4(13) | 3403(3) | 1921.5(19) | 13.8(6) |
| Na1 | 7050.9(7) | 1068.2(14) | 3531.6(9) | 15.4(3) |
| Na2 | 7073.6(6) | 3795.3(14) | 4350.3(9) | 15.2(3) |
| O101 | 7646.3(12) | −1143(2) | 2891.8(16) | 15.9(5) |
| O102 | 8466.7(12) | −1612(3) | 402.4(17) | 20.4(6) |
| O103 | 6627.3(12) | 1053(3) | 607.7(16) | 18.1(5) |
| O104 | 6344.0(12) | 3341(3) | 1758.8(18) | 19.5(5) |
| O105 | 6427.2(11) | 2343(3) | 3269.3(17) | 19.1(6) |
| O106 | 5682.7(13) | 55(3) | 3273.5(17) | 20.1(5) |
| O201 | 6876.5(11) | 5605(2) | 3330.9(15) | 13.7(5) |
| O202 | 6067.3(13) | 7005(3) | 384.5(17) | 20.3(6) |
| O203 | 7743.5(11) | 3535(2) | 3311.1(15) | 13.1(5) |
| O204 | 8471.3(12) | 1289(2) | 2836.7(17) | 16.3(5) |
| O205 | 8688.1(12) | 1844(3) | 1359.0(16) | 16.8(5) |
| O206 | 9113.6(13) | 4686(3) | 1422.1(17) | 19.6(6) |
| S101 | 6342.1(4) | 2128.0(9) | 2302.8(6) | 12.21(16) |
| S201 | 8552.4(4) | 2342.2(8) | 2194.3(6) | 11.75(16) |
| O1W | 7671.6(14) | 3233(3) | −27.4(18) | 22.5(6) |

As described herein, these problems and others in this area are addressed by the invention described herein, Thus, the scope of the invention shall include all modifications and variations that may fall within the scope of the attached claims. Other embodiments of the invention will be apparent to those skilled in the art from consideration of the specification and practice of the invention disclosed herein. it is intended that the specification and examples be considered as exemplary only, with a true scope and spirit of the invention being in heated by the following claims.

What is claimed is:

1. A hemihydrate flucarbazone sodium having the following X-ray crystal structure:

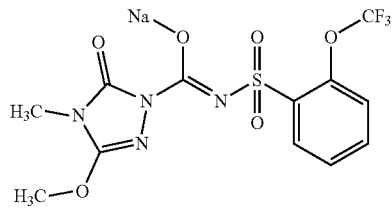

0.5 $H_2O$ having fractional atomic coordinates (×10⁴) and equivalent isotropic displacement parameters ($Å^2 \times 10^3$) as shown in the Table below; Ueq defined as ⅓ of the trace of the orthogonalised Uij and

| Atom | x | y | z | $U_{eq}$ |
|---|---|---|---|---|
| C101 | 7718.9(16) | −994(3) | 2120(2) | 14.0(7) |
| C102 | 8079.6(17) | −1177(4) | 875(2) | 15.8(7) |
| C103 | 8630.7(18) | −2451(4) | 2266(3) | 23.3(8) |
| C104 | 8399.4(19) | −992(5) | −487(3) | 28.7(9) |
| C105 | 6902.3(15) | 685(4) | 1355(2) | 12.9(6) |
| C106 | 5630.9(15) | 1357(3) | 1901(2) | 11.0(6) |
| C107 | 5328.5(16) | 1700(4) | 1027(2) | 16.3(7) |
| C108 | 4772.3(18) | 1138(5) | 674(3) | 26.1(9) |
| C109 | 4522.6(19) | 217(5) | 1173(3) | 30.8(10) |
| C110 | 4818.1(19) | −147(4) | 2042(3) | 26.0(9) |
| C111 | 5368.2(17) | 439(4) | 2398(2) | 15.7(7) |
| C112 | 5457(2) | 533(4) | 3974(3) | 25.5(9) |
| C201 | 6962.4(15) | 5702(3) | 2567(2) | 12.1(6) |
| C202 | 6887.8(16) | 6303(3) | 1130(2) | 14.6(7) |
| C203 | 6189.5(17) | 7478(4) | 1990(3) | 20.8(8) |
| C204 | 6925(2) | 6662(4) | −391(3) | 25.3(9) |
| C205 | 7736.8(15) | 3907(3) | 2529(2) | 12.1(6) |
| C206 | 9176.6(15) | 3330(3) | 2760(2) | 12.2(6) |
| C207 | 9428.9(16) | 3063(4) | 3663(2) | 15.2(7) |
| C208 | 9923.4(18) | 3798(4) | 4103(3) | 21.8(8) |
| C209 | 10162.3(18) | 4828(4) | 3649(3) | 24.0(8) |
| C210 | 9900.1(17) | 5131(4) | 2753(3) | 20.5(8) |
| C211 | 9414.1(16) | 4378(4) | 2318(2) | 14.5(7) |
| C212 | 9412(2) | 4553(4) | 761(3) | 26.3(9) |
| F101 | 4955.3(16) | −118(3) | 4036(2) | 49.8(8) |
| F102 | 5862.2(14) | 343(3) | 4726.0(17) | 44.9(8) |
| F103 | 5317.8(11) | 1848(2) | 3904.8(15) | 26.1(5) |
| F201 | 9798.1(16) | 5577(3) | 757.4(19) | 52.2(9) |
| F202 | 9024.3(14) | 4579(3) | −24.0(16) | 39.1(7) |
| F203 | 9724.6(13) | 3390(3) | 813.7(18) | 36.7(6) |
| N101 | 8155.3(14) | −1600(3) | 1755(2) | 14.8(6) |
| N102 | 7626.6(13) | −375(3) | 611.3(19) | 13.8(6) |
| N103 | 7395.7(13) | −235(3) | 1397.9(19) | 13.3(6) |
| N104 | 6833.4(13) | 1007(3) | 2197.5(19) | 13.7(6) |
| N201 | 6660.1(14) | 6540(3) | 1884(2) | 14.0(6) |
| N202 | 7311.2(13) | 5408(3) | 1247.9(18) | 13.1(6) |
| N203 | 7378,5(13) | 5041(3) | 2171.6(18) | 113(6) |
| N204 | 8028.4(13) | 3403(3) | 1921.5(19) | 13.8(6) |
| Na1 | 7050.9(7) | 1068.2(14) | 3531.6(9) | 15.4(3) |
| Na2 | 7073.6(6) | 3795.3(14) | 4350.3(9) | 15.2(3) |
| O101 | 7646.3(12) | −1143(2) | 2891.8(16) | 15.9(5) |
| O102 | 8466.7(12) | −1612(3) | 402.4(17) | 20.4(6) |
| O103 | 6627.3(12) | 1053(3) | 607.7(16) | 18.1(5) |
| O104 | 6344.0(12) | 3341(3) | 1758.8(18) | 19.5(5) |
| O105 | 6427.2(11) | 2343(3) | 3269.3(17) | 19.1(6) |
| O106 | 5682.7(13) | 55(3) | 3273.5(17) | 20.1(5) |
| O201 | 6876.5(11) | 5605(2) | 3330.9(15) | 13.7(5) |
| O202 | 6067.3(13) | 7005(3) | 384.5(17) | 20.3(6) |
| O203 | 7743.5(11) | 3535(2) | 3311.1(15) | 13.1(5) |
| O204 | 8471.3(12) | 1289(2) | 2836.7(17) | 16.3(5) |
| O205 | 8688.1(12) | 1844(3) | 1359.0(16) | 16.8(5) |
| O206 | 9113.6(13) | 4686(3) | 1422.1(17) | 19.6(6) |
| S101 | 6342.1(4) | 2128.0(9) | 2302.8(6) | 12.21(16) |
| S201 | 8552.4(4) | 2342.2(8) | 2194.3(6) | 11.75(16) |
| O1W | 7671.6(14) | 3233(3) | −27.4(18) | 22.5(6). |

* * * * *